United States Patent
Yacoub et al.

(10) Patent No.: US 11,786,888 B2
(45) Date of Patent: Oct. 17, 2023

(54) ELECTROACTIVE COMPOSITE COMPRISING GRAPHENE, A METALLOPROTEIN AND A CONJUGATE POLYMER

(71) Applicant: Heart Biotech Nano Limited, London (GB)

(72) Inventors: Magdi Habib Yacoub, London (GB); Mohammed Al Kordi, London (GB)

(73) Assignee: HEART BIOTECH NANO LIMITED, Winchester (GB)

( * ) Notice: Subject to any disclaimer, the term of this patent is extended or adjusted under 35 U.S.C. 154(b) by 862 days.

(21) Appl. No.: 16/606,369

(22) PCT Filed: Apr. 19, 2018

(86) PCT No.: PCT/GB2018/051030
§ 371 (c)(1),
(2) Date: Oct. 18, 2019

(87) PCT Pub. No.: WO2018/193259
PCT Pub. Date: Oct. 25, 2018

(65) Prior Publication Data
US 2022/0176359 A1 Jun. 9, 2022

(30) Foreign Application Priority Data
Apr. 20, 2017 (GB) .................... 1706313

(51) Int. Cl.
*B01J 31/00* (2006.01)
*B01J 21/18* (2006.01)
*C08G 61/12* (2006.01)

(52) U.S. Cl.
CPC ............ *B01J 31/003* (2013.01); *B01J 21/18* (2013.01); *C08G 61/123* (2013.01); *C08G 2261/3221* (2013.01); *C08G 2261/3228* (2013.01); *C08G 2261/344* (2013.01)

(58) Field of Classification Search
CPC ....... B01J 31/003; B01J 21/18; C08G 61/123; C08G 2261/3221; C08G 2261/3228; C08G 2261/344
See application file for complete search history.

(56) References Cited

FOREIGN PATENT DOCUMENTS

| | | |
|---|---|---|
| CN | 103923304 A | 7/2014 |
| CN | 104977337 A | 10/2015 |
| CN | 105572188 A | 5/2016 |
| WO | 2015015386 A1 | 2/2015 |

OTHER PUBLICATIONS

International Search Report and Written Opinion dated Aug. 2, 2018 for corresponding International Patent Application No. PCT/GB2018/051030.

(Continued)

*Primary Examiner* — Shane Fang
(74) *Attorney, Agent, or Firm* — TAROLLI, SUNDHEIM, COVELL & TUMMINO L.L.P.

(57) ABSTRACT

The present invention provides a composite comprising graphene, a conjugated porous organic polymer and a metalloprotein and to methods of making the composite. The invention also relates to articles (e.g. to an electrode) comprising the composite and to uses of the composite, e.g. in heterogeneous catalysis of oxygen reduction reactions, and in oxygen sensing.

20 Claims, 9 Drawing Sheets

(56) References Cited

OTHER PUBLICATIONS

Junhua Wei et al., "A reduced graphene oxide based electrochemical biosensor for tyrosine detection", Nanotechnology, IOP, Bristol GB, vol. 23, No. 33, p. 335707.
Chen R.J., et., "Noncovalent Sidewall Functionalisation of Single-Walled Carbon Nanotubes for Protein Immobilisation" Journal of the American Chemical Society, vol. 123, p. 3838-3839.
Kungping Liu et al., "Direct electrochemistry amd electrocatalysis of hemoglobin based on poly (diallyldimethylammonium chloride) functionalised graphene sheets/room temperature ionic liquid composite film" Electrochemistry Communications, vol. 12, No. 3, p. 402-405.

ELECTROACTIVE COMPOSITE COMPRISING GRAPHENE, A METALLOPROTEIN AND A CONJUGATE POLYMER

RELATED APPLICATIONS

The present application is a U.S. National Stage application under 35 USC 371 of PCT Application Serial No. PCT/GB2018/051030, filed on 19 Apr. 2018; which claims priority from GB Patent Application No. 1706313.2, filed 20 Apr. 2017, the entirety of all of which are incorporated herein by reference.

The present invention relates to a composite comprising graphene, a conjugated porous organic polymer and a metalloprotein and to methods of making the composite. The invention also relates to articles (e.g. to an electrode) comprising the composite and to uses of the composite, e.g. in heterogeneous catalysis of oxygen reduction reactions, and in oxygen sensing.

BACKGROUND

Porous organic polymers have emerged as a useful class of materials owing to their rigid structures, high thermal and chemical stabilities, low densities, and in certain cases, their permanent porosity and relatively high surface area. Porous organic polymers can be synthesised through "bottom-up" assembly, wherein monomers are selected to achieve a desired polymer framework and/or topology. Several synthetic pathways have been employed in the synthesis of porous organic polymers including (i) boronic acid condensation, (ii) imine formation, (iii) Sonogashira-Hagihara cross-coupling, (iv) triazine synthesis via nitrile trimerisation, and (v) cobalt-catalysed acetylene trimerisation.

Porous organic polymers comprising different monomers are particularly interesting because of the option to fine tune the polymer properties towards specific applications. One common strategy that has been employed is framework decoration. In framework decoration, functional groups which do not interfere with the polymer framework bond forming process are included in the monomers, thus providing functionalised polymer to meet specific applications. This technique allows the construction of porous organic polymers containing one or multiple type(s) of chemical functionalities, simultaneously integrated into the polymer framework. Combinations of different monomers have also been used to construct porous organic polymers with specified pore sizes and volumes and surface areas. Such polymers are interesting in applications such as gas capture, gas separation and heterogeneous catalysis. By employing a combination of these strategies, attempts have been made to develop porous organic polymers with substrate-specific pores.

During assembly of the polymer framework, monomers may be selected to create pores and/or functional groups to promote trapping of substrate molecules within, or on the surface of, the polymer framework. Substrate molecules are therefore absorbed and/or adsorbed into the polymer framework, providing a large substrate concentration over a given geometric surface area. As such, the porous organic polymer can act as a "reservoir" of molecules. The trapped substrate molecules are then readily available for chemical reactions which are catalysed by the polymer.

One limitation of porous organic polymers is their low electrical conductivity. This restricts the application of the polymers in heterogeneous catalysis to thermally driven conversion processes. Attempts to improve the electrical properties of porous organic polymers have included, for example, doping with metal ions. However, the electrical conductivity of such porous organic polymers still requires improvement.

SUMMARY

Viewed from a first aspect, the present invention provides a composite comprising graphene, a metalloprotein and a conjugated porous organic polymer.

Viewed from a further aspect, the present invention provides a method of making a composite as hereinbefore defined comprising: mixing graphene, a metalloprotein and a conjugated porous organic polymer.

Viewed from a further aspect, the present invention provides an article comprising a composite as hereinbefore defined.

Viewed from a further aspect, the present invention provides a medical device comprising an electrode which comprises a composite as hereinbefore defined.

Viewed from a further aspect, the present invention provides a use of a composite as hereinbefore defined for gas sensing and electrochemical heterogeneous catalysis.

Viewed from a further aspect, the present invention provides a use of a composite as hereinbefore defined for catalysing oxygen reduction reactions.

Viewed from a further aspect, the present invention provides a method of catalysing an oxygen reduction reaction comprising: bringing a material to be oxidised into contact with an electrode comprising a composite as hereinbefore described.

Definitions

As used herein the term "conjugated porous organic polymer" refers to polymers having pi-conjugation throughout their network or system and which comprise rigid monomers (e.g. alkyne-comprising monomers) giving rise to porosity.

As used herein the term "metalloprotein" refers to a protein having an active site comprising a metal. Preferred metalloproteins are metalloenzymes.

As used herein the term "aromatic ring" refers to a planar ring that has 4n+2 pi electrons, wherein n is a non-negative, non-zero integer.

As used herein the term "aromatic ring system" refers to groups of two or more aromatic rings wherein the rings are fused or bonded directly.

As used herein the term "heteroaromatic ring" refers to an aromatic ring in which one or more ring carbon atoms are replaced by at least one hetero atom such as —O—, —N— or —S—.

As used herein the term "alkynyl" refers to straight chained, branched or cyclic groups comprising a triple bond. Alkynyl groups may be substituted or unsubstituted. As used herein the term "alkyl" refers to saturated, straight chained, branched or cyclic groups. Alkyl groups may be substituted or unsubstituted.

As used herein the term "halide" refers to atoms selected from the group consisting of F, Cl, Br and I. Preferred halides are Br, Cl and I and especially Br.

DETAILED DESCRIPTION OF THE INVENTION

The present invention relates to a composite comprising graphene, a metalloprotein and a conjugated porous organic polymer. The composite comprises a myriad of different properties. The relatively rigid and porous structure of the conjugated porous organic polymer enables the composite to host a relatively large molecule, namely a metalloprotein, within its structure and which can, for example, provide catalytic properties. The graphene provides high levels of electrical conductivity. Advantageously the combination of the metalloprotein and the graphene in the conjugated porous organic polymer enables the composite to be employed in a range of electrochemical heterogeneous catalysis reactions.

In preferred composites of the present invention the conjugated porous organic polymer is uniformly distributed on the surface of the graphene. Thus preferably the conjugated porous organic polymer forms a layer on the surface of the graphene. This is facilitated by pi-pi electron interactions between the graphene and the polymer. Preferably the metalloprotein is encapsulated in the composite and still more preferably the metalloprotein is encapsulated in the conjugated porous organic polymer in the composite. The encasing of the metalloprotein in the composite provides physical stability to the metalloprotein within the composite. Still more preferably the metalloprotein is trapped in the composite.

In preferred composites of the present invention the conjugated porous organic polymer comprises a repeat unit of formula (I):

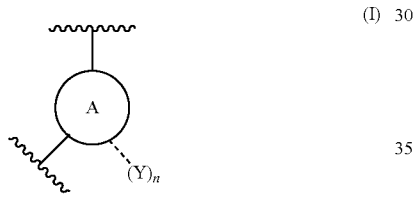

wherein
A is an aromatic ring or ring system;
---- represents a bond which may be present or absent;
each Y is independently selected from ~~~, CHO, COR, COOR, COOH, NH$_2$, NHR, NR$_2$, CONH, CONHR wherein R is C$_{1-8}$ alkyl, OH, phenol, halide, aryl or heteroaryl; and
n is 0 or an integer between 1 and 4.

In preferred repeat units of formula (I), ---- is present. When ---- is present, n is preferably 1 and Y is ~~~. In other words the repeat unit (I) preferably has three growing branches. Alternatively, when ---- is present and n is 1, Y is CHO, COR, COOR, COOH, NH$_2$, NHR, NR$_2$, CONH, CONHR wherein R is C$_{1-8}$ alkyl, OH, phenol, halide, aryl or heteroaryl. These groups provide functionality in the polymer for post-polymerisation modifications.

In preferred composites of the present invention the conjugated porous organic polymer comprises a repeat unit derived from a monomer of formula (II):

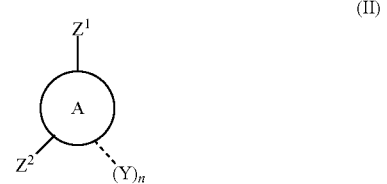

wherein
A is an aromatic ring or an aromatic ring system;
$Z^1$ is alkynyl;
$Z^2$ is selected from alkynyl, halide, OH and OTf and preferably alkynyl;
---- is a bond which may be present or absent;
each Y is independently selected from alkynyl, halide, OH, OTf, CHO, COR, COOR, COOH, NH$_2$, NHR, NR$_2$, CONH, CONHR wherein R is C$_{1-8}$ alkyl, OH, phenol, halide, aryl or heteroaryl; and
n is 0 or an integer between 1 and 4.

In preferred repeat units and monomers of formulae (I) and (II) respectively, A is an aromatic ring. Preferred aromatic rings are 5 or 6 membered aromatic rings. The aromatic ring may be non-heteroaromatic or heteroaromatic, but is preferably non-heteroaromatic. A particularly preferred aromatic ring is benzene.

When A is an aromatic ring system, the ring system may comprise 2 to 6 rings, more preferably 2 to 4 rings, and still more preferably 2 or 3 rings. The individual rings in the aromatic ring system may be fused or non-fused or a mixture thereof. Preferably the rings are non-fused. Representative examples of aromatic ring systems are shown below:

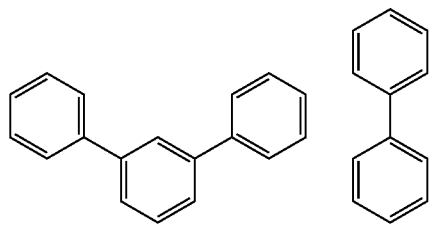

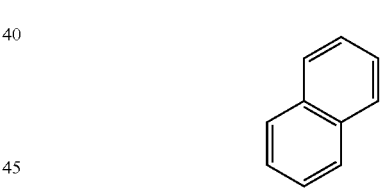

In preferred monomers of formula (II), ---- is present. Preferably n is 1 or 2, and more preferably 1. When n is 2, one Y is preferably alkynyl, halide (preferably Br, Cl or I and more preferably Br), OH or OTf and one Y is selected from CHO, COR, COOR, COOH, NH$_2$, NHR, NR$_2$, CONH, CONHR wherein R is C$_{1-8}$ alkyl, OH, phenol, halide, aryl or heteroaryl. When n is 1, Y is preferably alkynyl, halide (preferably Br, Cl or I and more preferably Br), OH or OTf and more preferably alkynyl.

In preferred monomers of formula (II), $Z^1$, $Z^2$ and Y are all the same and still more preferably $Z^1$, $Z^2$ and Y are all alkynyl.

In preferred monomers of formula (II), $Z^1$ and $Z^2$ are present in a meta or para arrangement, preferably a meta arrangement.

Particularly preferred monomers of formula (II) are monomers (IIa), (IIb) and (IIc) shown below. Monomer (IIa) is particularly preferred.

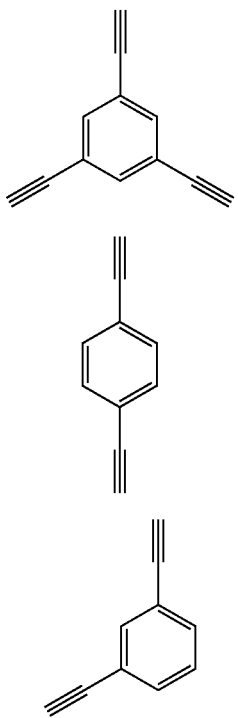

(IIa)

(IIb)

(IIc)

The conjugated porous organic polymer present in the composite of the present invention preferably comprises 1, 2 or 3 different monomers, preferably 1 or 2 monomers and still more preferably 1 monomer of formula (II).

Further preferred conjugated porous organic polymers present in the composite of the present invention comprise a repeat unit of formula (III):

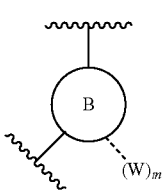

(III)

wherein
B is an aromatic ring or ring system;
---- represents a bond which may be present or absent;
W is selected from ~~~, CHO, COR, COOR, COOH, NH$_2$, NHR, NR$_2$, CONH, CONHR wherein R is C$_{1-8}$ alkyl, OH, phenol, halide, aryl or heteroaryl; and
m is 0 or an integer between 1 and 4

In some preferred repeat units of formula (III), ---- is absent.

In other preferred repeat units of formula (III), ---- is present. When ---- is present, m is preferably 1 and W is ~~~. In other words, the monomer (III) preferably has three growing branches. Alternatively, when ---- is present and m is 1, W is CHO, COR, COOR, COOH, NH$_2$, NHR, NR$_2$, CONH, CONHR wherein R is C$_{1-8}$ alkyl, OH, phenol, halide, aryl or heteroaryl. These groups provide functionality in the polymer for post-polymerisation modifications.

In preferred composites of the present invention the conjugated porous organic polymer further comprises a repeat unit derived from a monomer of formula (IV):

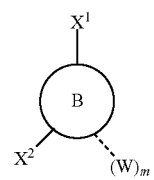

(IV)

wherein
B is an aromatic ring or ring system;
X$^1$ is selected from halide, OH and OTf;
X$^2$ is selected from halide, OH, OTf and alkynyl, preferably halide, OH or OTf;
---- is a bond which is present or absent;
each W is independently selected from alkynyl, halide, OH, OTf, CHO, COR, COOR, COOH, NH$_2$, NHR, NR$_2$, CONH, CONHR wherein R is C$_{1-8}$ alkyl, OH, phenol, halide, aryl or heteroaryl; and
m is 0 or an integer between 1 and 4.

In preferred repeat units and monomers of formulae (III) and (IV) respectively, B is an aromatic ring. Preferred aromatic rings are 5 or 6 membered aromatic rings. The aromatic ring may be non-heteroaromatic or heteroaromatic. Representative examples of suitable aromatic rings include benzene, pyridine, pyrimidine, pyridazine, pyrazine and triazine. When B is non-heteroaromatic, it is preferably benzene. When B is heteroaromatic it is preferably selected from pyridine, pyrimidine, pyridazine, pyrazine and triazine and still more preferably pyridine or pyrmidine and particularly pyrimidine.

When B is an aromatic ring system, the ring system may comprise 2 to 6 rings, more preferably 2 to 4 rings, and still more preferably 2 or 3 rings. The individual rings in the aromatic ring system may be fused or non-fused or a mixture thereof. Preferably the rings are non-fused. Representative examples of aromatic ring systems are as shown above in relation to ring A.

In some preferred monomers of formula (IV), ---- is absent and m is 0.

In other preferred monomers of formula (IV), ---- is present. Preferably m is 1 or 2, and more preferably 1. When m is 2, one W is preferably alkynyl, halide (preferably Br, Cl or I and more preferably Br), OH or OTf and one W is selected from CHO, COR, COOR, COOH, NH$_2$, NHR, NR$_2$, CONH, CONHR wherein R is C$_{1-8}$ alkyl, OH, phenol, halide, aryl or heteroaryl. When m is 1, W is preferably alkynyl, halide (preferably Br, Cl or I and more preferably Br), OH or OTf, more preferably halide (preferably Br, Cl or I and more preferably Br), OH or OTf and still more preferably halide, preferably Br, Cl or I and more preferably Br.

In preferred monomers of formula (IV), X$^1$ and X$^2$ are the same and still more preferably X$^1$ and X$^2$ are selected from halide (preferably Br, Cl or I and more preferably Br), OH and OTf, and particularly halide, preferably Br, Cl or I and more preferably Br. Still more preferably $X^1$, $X^2$ and W are the same and still further preferably $X^1$, $X^2$ and W are selected from halide (preferably Br, Cl or I and more preferably Br), OH and OTf and particularly halide, preferably Br, Cl or I and more preferably Br.

In preferred monomers of formula (IV), $X^1$ and $X^2$ are present in a meta or para arrangement and preferably a meta arrangement.

Particularly preferred monomers of formula (IV) are monomers (IVa), (IVb), (IVc) or (IVd) are shown below. Monomers (IVa) and (IVb) are particularly preferred.

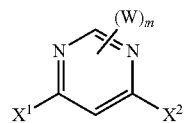
(IVa)

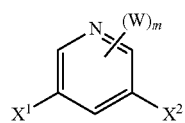
(IVb)

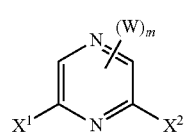
(IVc)

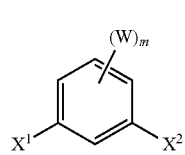
(IVd)

wherein $X^1$, $X^2$, W and m are as defined above in relation to formula (IV).

In preferred monomers of formulae (IVa)-(IVd), m is 0 or 1 and still more preferably 0.

In further preferred monomers of formulae (IVa)-(IVd), $X^1$ and $X^2$ are selected from halide (preferably Br, Cl or I and more preferably Br), OH and OTf and more preferably halide, preferably Br, Cl or I and more preferably Br.

A particularly preferred monomer of formula (IV) is:

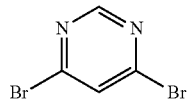

The conjugated porous organic polymer present in the composite of the present invention preferably comprises 1, 2 or 3 different monomers, preferably 1 or 2 monomers and still more preferably 1 monomer of formula (IV).

Particularly preferably the composite of the present invention comprises a conjugated porous organic polymer comprising a repeat unit of formula (V):

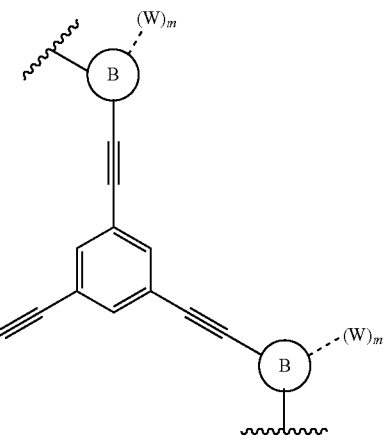
(V)

wherein B, ----, W and m are as defined above in relation to formula (III).

In some preferred repeat units of formula (V), ---- is absent.

In other preferred repeat units of formula (V), ---- is present on each ring B. When ---- is present, m is preferably 1 and W is ∿. Alternatively, when ---- is present and m is 1, W is CHO, COR, COOR, COOH, $NH_2$, NHR, $NR_2$, CONH, CONHR wherein R is $C_{1-8}$ alkyl, OH, phenol, halide, aryl or heteroaryl. These groups provide functionality in the polymer for post-polymerisation modifications.

In preferred repeat units of formula (V), B is an aromatic ring. Preferred aromatic rings are 5 or 6 membered aromatic rings. The aromatic ring may be non-heteroaromatic or heteroaromatic. Representative examples of suitable aromatic rings include benzene, pyridine, pyrimidine, pyridazine, pyrazine and triazine. When B is non-heteroaromatic, it is preferably benzene. When B is heteroaromatic it is preferably selected from pyridine, pyrimidine, pyridazine, pyrazine and triazine and still more preferably pyridine or pyrmidine and particularly pyrimidine.

When B is an aromatic ring system, the ring system may comprise 2 to 6 rings, more preferably 2 to 4 rings, and still more preferably 2 or 3 rings. The individual rings in the aromatic ring system may be fused or non-fused or a mixture thereof. Preferably the rings are non-fused. Representative examples of aromatic ring systems are as shown above in relation to ring A.

A particularly preferred repeat unit of formula (V) is formula (Va) shown below:

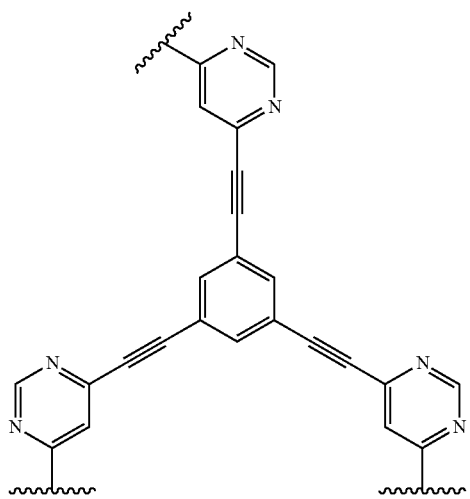

(Va)

In some composites of the present invention the conjugated porous organic polymer further comprises a unit derived from a compound of formula (VI):

(VI)

wherein
C is an aromatic ring or ring system;
U is selected from halide, OH and OTf;
---- is a bond which may be present or absent;
each V is independently selected from CHO, COR, COOR, COOH, $NH_2$, NHR, $NR_2$, CONH, CONHR wherein R is $C_{1-8}$ alkyl, OH, phenol, halide, aryl or heteroaryl; and o is 0 or an integer between 1 and 4.

In preferred compounds of formula (VI), o is 1.

In preferred compounds of formula (VI), V is selected from CHO, COR, COOR, COOH, $NH_2$, NHR, $NR_2$, CONH, CONHR wherein R is $C_{1-8}$ alkyl, OH, phenol, halide, aryl or heteroaryl. These groups introduce functionality into the polymer that may be used for post-polymerisation modification.

In preferred compounds of formula (VI), U is halide, preferably Br, Cl or I and more preferably Br. In further preferred compounds of formula (VI), U and V are present in a meta or para arrangement.

In compounds of formula (VI), C is preferably an aromatic ring. Preferred aromatic rings are 5 or 6 membered aromatic rings. The aromatic ring may be non-heteroaromatic or heteroaromatic. Representative examples of suitable aromatic rings include benzene, pyridine, pyrimidine, pyridazine, pyrazine and triazine. When C is non-heteroaromatic, it is preferably benzene. When C is heteroaromatic it is preferably selected from pyridine, pyrimidine, pyridazine, pyrazine and triazine and still more preferably pyridine or pyrmidine and particularly pyrimidine.

When C is an aromatic ring system, the ring system may comprise 2 to 6 rings, more preferably 2 to 4 rings, and still more preferably 2 or 3 rings. The individual rings in the aromatic ring system may be fused or non-fused or a mixture thereof. Preferably the rings are non-fused. Representative examples of aromatic ring systems are as shown above in relation to ring A.

Particularly preferred compounds of formula (VI) are compounds (VIa), (VIb), (VIc) and (VId), and particularly unit (VId), shown below:

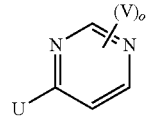

(VIa)

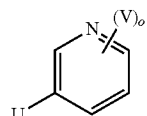

(VIb)

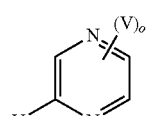

(VIc)

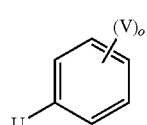

(VId)

wherein U, V and o are as defined above in relation to formula (VI).

Still further preferred compounds of formula (VI) are those of formula (VIe):

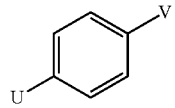

(VIe)

wherein U and V are as defined in relation to formula (VI).

In preferred compounds of formula (VIa)-(VIe), U is preferably halide, preferably Br, Cl or I and more preferably Br.

The conjugated porous organic polymer present in the composite of the present invention preferably comprises 1, 2 or 3 different compounds, preferably 1 or 2 compounds and still more preferably 1 compound of formula (VI).

The conjugated porous organic polymer present in the composite of the present invention preferably comprises monomers of formula (II) and (IV) in a weight ratio of 1:1 to 3:1, more preferably 1.1:1 to 2:1 and still more preferably 1.2:1 to 1.5:1. The conjugated porous organic polymer present in the composite of the present invention preferably comprises a monomer of formula (II) and a compound of formula (VI) in a weight ratio of 1:1 to 1.5:1, more preferably 1.2:1 to 1.4:1 and still more preferably 1.1:1 to 1:1.

The conjugated porous organic polymer present in the composite of the present invention preferably comprises repeat units derived from monomers of formula (II) in an amount of 10-80% wt, more preferably 20-60% wt and still more preferably 25-50% wt, based on the total weight of the polymer. The conjugated porous organic polymer present in the composite of the present invention preferably comprises repeat units derived from monomers of formula (IV) in an amount of 5-70% wt, more preferably 10-50% wt and still more preferably 20-50% wt, based on the total weight of the polymer.

The conjugated porous organic polymer present in the composite of the present invention preferably comprises units derived from monomers of formula (VI) in an amount of 5-70% wt, more preferably 10-50% wt and still more preferably 20-50% wt, based on the total weight of the polymer.

The conjugated porous organic polymer present in the composite of the present invention preferably has a surface area of 100 to 1500 $cm^2/g$, more preferably 150 to 1000 $cm^2/g$ and still more preferably 200 to 800 $cm^2/g$. The conjugated porous organic polymer preferably has a 3D network. Preferably the conjugated porous organic polymer is amorphous.

The composite of the present invention also comprises graphene. The graphene present in the composition preferably has an average particle size of 10 nm to 500 micron, more preferably 20 nm to 250 micron and still more preferably 50 nm to 50 micron. The graphene present in the composition preferably has a surface area of 50 to 1000 $m^2/g$, more preferably 100 to 900 $m^2/g$ and still more preferably 150 to 800 $m^2/g$. Preferably the graphene is non-functionalised. Preferably the graphene is in reduced form, i.e. not in oxidised form. Preferably the graphene is non-modified graphene. Suitable graphene is commercially available.

The composite of the present invention also comprises a metalloprotein. Preferably the metalloprotein is a metalloenzyme and particularly preferably a haemoprotein. Still more preferably the metalloprotein is haemoglobin and in particular human haemoglobin.

Preferred composites of the present invention comprise 40 to 80 wt %, more preferably 45 to 75 wt % and still more preferably 50 to 70 wt % conjugated porous organic polymer, based on the total weight of the composite. Preferred composites of the present invention comprise 10 to 45 wt %, more preferably 15 to 40 wt % and still more preferably 20 to 35 wt % graphene, based on the total weight of the composite.

Preferred composites of the present invention comprise 2 to 30 wt %, more preferably 5 to 25 wt % and still more preferably 10 to 20 wt % metalloprotein, based on the total weight of the composite.

Preferred composites of the present invention comprise conjugated porous organic polymer and graphene in a weight ratio of 5:1 to 1:1, more preferably 3:1 to 1:1 and still more preferably 2.5:1 to 1:1. Preferred composites of the present invention comprise conjugated porous organic polymer to metalloprotein in a weight ratio of 8:1 to 2:1, more preferably 6:1 to 2.5:1 and still more preferably 5:1 to 3:1.

Preferred composites of the invention have an average pore diameter of 5 to 70 Angstrom, more preferably 25 to 60 Angstrom and still more preferably 40 to 60 Angstrom. Preferably the composite has substantially no pores with a diameter of 70 Angstrom or greater and substantially no pores with a diameter of 75 Angstrom or greater. This is believed to be because the metalloprotein occupies the largest pores of the porous network.

Preferred composites of the present invention conduct ions and/or electricity. Preferably the conjugated porous organic polymer and the graphene both contribute to the conductivity of the composite.

The composite of the present invention is preferably prepared by mixing graphene, a metalloprotein and the precursors for a conjugated porous organic polymer. The synthesis of conjugated porous organic polymers is well known in the art. Top Curr Chem (2010) 293:1-33 and Adv. Mater. 2009, 21, 1291-1295 both provide a review of several classes of conjugated porous organic polymers and an overview of their synthesis. The skilled person is therefore clearly aware of the precursors needs to prepare any given conjugated porous organic polymer. Suitable graphene and metalloprotein (e.g. haemoglobin) may be purchased commercially. Suitable conjugated porous organic polymer may also be purchased commercially.

More preferably, however, the conjugated porous organic polymer is synthesised in situ in the mixture, preferably by a Sonogashira-Hagihra reaction. Conventional Sonogashira-Hagihra conditions may be employed, with the exception that graphene and metalloprotein are additionally present in the reaction mixture. The Sonogashira-Hagihra reaction may be utilised for the preparation of a range of conjugated porous organic polymers.

Preferably therefore the composite of the present invention is prepared by a method comprising:
mixing graphene, a metalloprotein and monomers for the preparation of a conjugated porous organic polymer (e.g. monomers of formulae (II) and (IV) and optionally compounds of formula (VI)) in the presence of a catalyst to form a composite; and obtaining said composite.

Preferably the monomers employed in the method of the invention are monomers of formulae (II) and (IV) as hereinbefore defined. Preferred monomers of formula (II) are as defined above. Preferred monomers of formula (IV) are as defined above. Some preferred methods of the present invention, further comprise mixing a compound of formula (VI) with the graphene, metalloprotein and afore-mentioned monomers.

The catalyst employed in the method of the invention preferably comprises palladium and optionally copper. Preferably the palladium is in the form of a palladium (0) complex. Representative examples of suitable palladium complexes include $(Ph_3P)_2PdCl_2$, $Pd(PPh_3)_4$, $NaPdCl_4$, $Pd(OAc)_2$, $Pd(MeCN)_2Cl_2$, $PdCl_2$, $PdI_2$, $[Pd(allyl)Cl_2]_2$, $Pd(TFA)_2$, $Pd(PCy_3)_2Cl_2$, $PdBr_2$ and PdPEPPSI-iPr. Preferably the palladium catalyst is selected from $(Ph_3P)_2PdCl_2$ and $Pd(PPh_3)_4$.

The copper catalyst is preferably a halide salt of copper (I). A representative example of a suitable copper salt is CuI.

In the method of the present invention, the graphene, a metalloprotein and monomers for the preparation of a conjugated porous organic polymer are preferably mixed in the presence of a base. Representative examples of suitable bases include amines (e.g. diethylamine, DBU, N-ethyldiisopropylamine, piperidine, diisopropylamine) potassium carbonate, cesium carbonate, sodium carbonate, $Bu_4NOAc$ and NaOAc. Amines are preferred and particularly triethylamine.

Optionally the base can also act as the reaction solvent. Alternatively the solvent may be selected from tetrahydrofuran, ethers, glycol ethers, dimethylsulfoxide, dimethylformamide, acetonitrile, acetamide, toluene, dimethylacetamide, dioxone and combinations thereof. A preferred solvent is DMF.

The other reaction conditions, e.g. temperature, time etc. are conventional and can readily be determined by the person skilled in the art.

The composite of the present invention may be used in a range of applications. Thus articles comprising a composite as hereinbefore described form a further aspect of the invention. A preferred article is an electrode. Miniature electrodes are particularly preferred. Electrodes may, for example, be formed from the composite or coated with the composite herein described. The electrodes may, in turn, be incorporated into medical devices, and in particular implantable medical devices. Thus medical devices comprising the composite hereinbefore described form another aspect of the invention.

The composite of the present invention may be advantageously used for gas sensing (e.g. oxygen sensing) and electrochemical heterogeneous catalysis, and most preferably electrochemical heterogeneous catalysis. The composite of the present invention is particularly useful for catalysing oxygen reduction reactions.

DETAILED DESCRIPTION OF THE FIGURES

The invention will now be described with reference to the following non-limiting examples and Figures, wherein.

EXAMPLES

Figure 1:
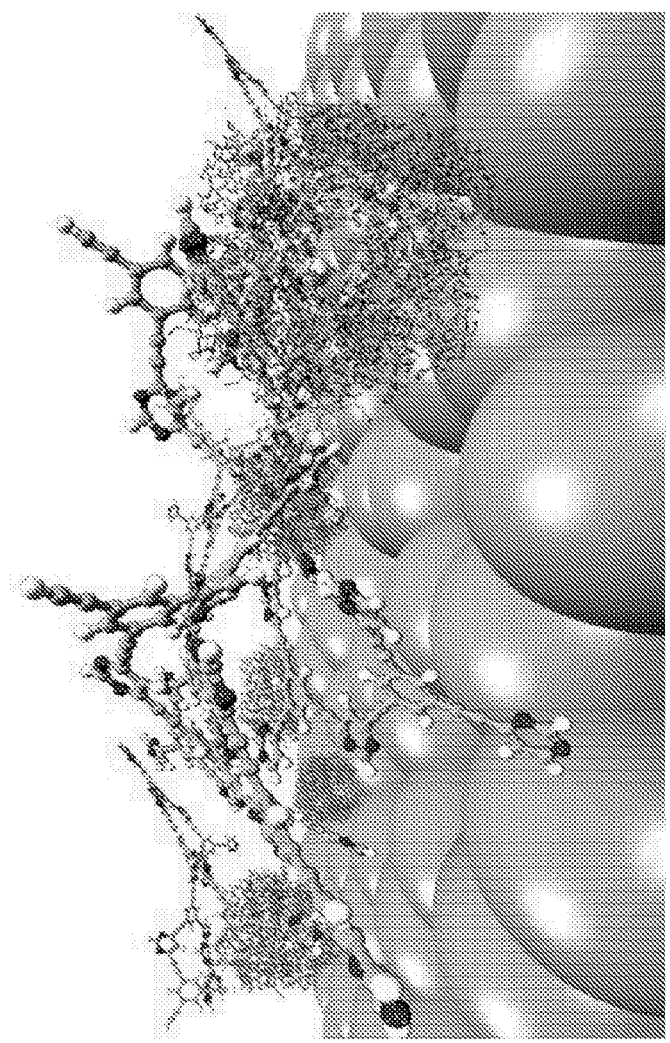
FIG. 1 is a schematic of the synthesis of a composite of the invention showing immobilisation of Hb on the PyPOP-graphene structure.
Figure 1:
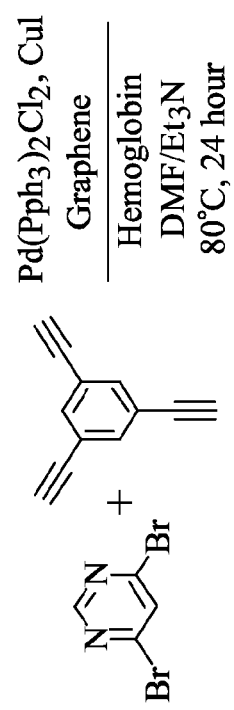

The examples were performed using the following materials and equipment, unless otherwise stated:

Chemicals: solvents, catalysts and chemicals were purchased from Sigma-Aldrich or Fisher Scientific UK. Brominated aromatics were purchased from Combi-blocks. Graphene was purchased from Alfa-Aesar and used without further purification. Nitrogen gas (99.999%) and carbon dioxide (99.995%) was purchased from Airliquide.

Biological reagents: Human haemoglobin was purchased as a lyophilized powder from Sigma-Aldrich and used without further purification.

Infrared absorption spectra were recorded using a Thermoscientific Nicoletis-10.

$^{13}$C NMR spectra were recorded on a 400 MHz SS NMR ADVANCE III spectrometer. $^{13}$C CP-MAS were recorded at a resonance frequency of 100 MHz under 13 kHz pining rate using a triple-resonance 4 mm Bruker MAS probe (BrukerBioSpin), at a temperature of 298 K. Cross-polarisation contact time was 2 ms employing ramp 100 for variable amplitude CP. To achieve a sufficient signal-to-noise ratio in a reasonable amount of time, 12 k transients and 24 k were collected with 7 s recycle delay. Exponential line broadening of 10 Hz applied before Fourier Transformation. Bruker Topspin 3.0 software was used for data collection and for spectral analysis.

Elemental analysis for Carbon, Hydrogen and Nitrogen content of samples was conducted using a ThermoScientific Flash 2000.

X-ray photoelectron spectroscopy (XPS) was conducted using a Kratos AXIS Ultra DLD XPS system with a hemispherical energy analyser, and a monochromatic Al Ka source operated at 15 keV and 150 W. The X-rays were incident at an angle of 45° with respect to the surface normal. Samples were placed in small powder sockets on the holder and analysis was performed at a pressure below $1 \times 10^{-9}$ mbar. High resolution core level spectra were measured with pass energy of 40 eV. The XPS experiments were performed using an electron beam directed onto the sample for charge neutralisation. Sample sputtering was performed under Ultra High Vacuum conditions using an ion gun mounted on the XPS analysis chamber. The $Ar^+$ ions were accelerated to beam energy of 4 keV and the raster size was selected at 6 mm×6 mm.

Scanning electron microscopy images were acquired on a JEOL JEM-2100 at 200 KV.

Gas sorption analysis was conducted on a Micrometrics ASAP2020. The variable temperate $CO_2$ isotherms were recorded in an insulated dewar connected to an LAUDA A-8 circulating chiller. The surface areas were determined from the nitrogen adsorption isotherms collected at 77 K by applying the Brunauer-Emmett-Teller and Langmuir models. Pore size analysis was conducted using a slit NLDFT pore model system by assuming a carbon finite pores surface.

Cyclic voltammetry CPE electrode were coated with PyPOP-Hb@G

Example 1

Synthesis of a conjugated porous-organic polymer and synthesis of a composite of the invention Pyrimide based porous organic polymer (PyPOP) was synthesised employing the following procedure: A solution of dimethylformamide (15 mL) and trimethylamine (2 mL) was degassed in a 100 mL pressure vial using the freeze-pump-thaw method for three cycles, and maintained under a nitrogen atmosphere. To the degassed solution was added 4,6-dibromopyrimidine (23 mg, 0.1 mmol), and 1,3,5-triethynylbenzene (15 mg, 0.1 mmol), and the vial sonicated for 30 minutes. Copper (I) iodide (5 mg, 0.026 mmol), triphenylphosphine (5 mg, 0.019 mmol) and $PdCl_2(PPh_3)_2$ (5 mg, 0.014 mmol) were then added, and the vial sealed under a flow of nitrogen. The reaction mixture was stirred at 80° C. for 24 hours. The resulting mixture was filtered under vacuum through a sintered glass funnel, and the solid washed with acetonitrile. The solid was then suspended in acetonitrile and stirred at 60° C. in a sealed vial for 6 hours, and filtered under vacuum as previously described. The resulting solid was dried at 110° C. for 5 minutes to afford PyPOP.

A PyPOP and graphene composite (POP@G) was synthesised using the procedure described above except that graphene powder (8 mg) was added to the reaction mixture at the same time as the brominated aromatics. The reaction yielded a dark olive-black solid (30 mg, 96% yield).

A composite of the present invention (PyPOP-Hb@G) was synthesised using the procedure as described above wherein the reaction mixture additionally comprised haemoglobin (5 mg) to afford PyPOP-Hb@G as a solid (33 mg).

Example 2

Infrared spectroscopy was used to confirm the presence of PyPOP and Hb in the PyPOP@G and PyPOP-Hb@G composites synthesised in Example 1.

Figure 2:
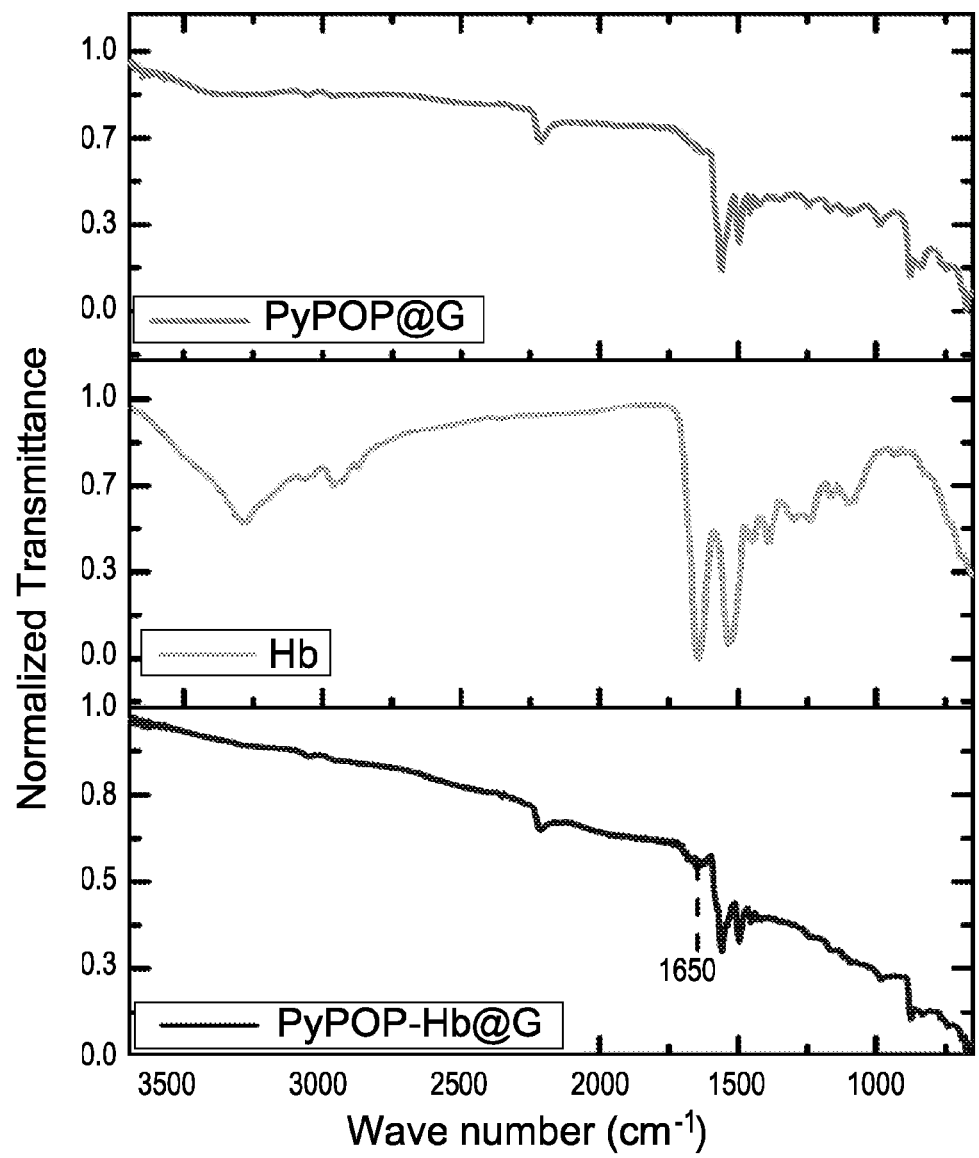
FIG. 2 shows the Infrared spectra of Hb as well as PyPOP@G and PyPOP-Hb@G composites synthesised in Example 1.

Analysis of the IR spectrum of PyPOP@G revealed the presence of stretch frequencies at 2215 cm$^{-1}$ and 1564 cm$^{-1}$, corresponding to the characteristic stretch frequency of a diaryl substituted alkyne ($v_{C≡C}$) and pyrimidine ($v_{C=N}$) respectively (FIG. 2). Notably, no peak was observed for an unsubstituted terminal alkyne ($v_{C-H}$~3200 cm$^{-1}$) indicating the cross coupling reaction as described in Example 1 was successful, and that PyPOP was successfully synthesised. A weak absorption peak at 1650 cm$^{-1}$ was also observed, and assigned to the amide ($v_{C=O}$) stretch frequency in Hb. This weak peak at 1650 cm$^{-1}$ was found to be absent in the IR spectrum of PyPOP@G, providing confidence in attributing the peak to Hb (FIG. 2).

Example 3

Solid State $^{13}$C-CPMAS NMR spectrometry was used to evaluate the presence of immobilised Hb in PyPOP-Hb@G synthesised in Example 1.

Figure 3:
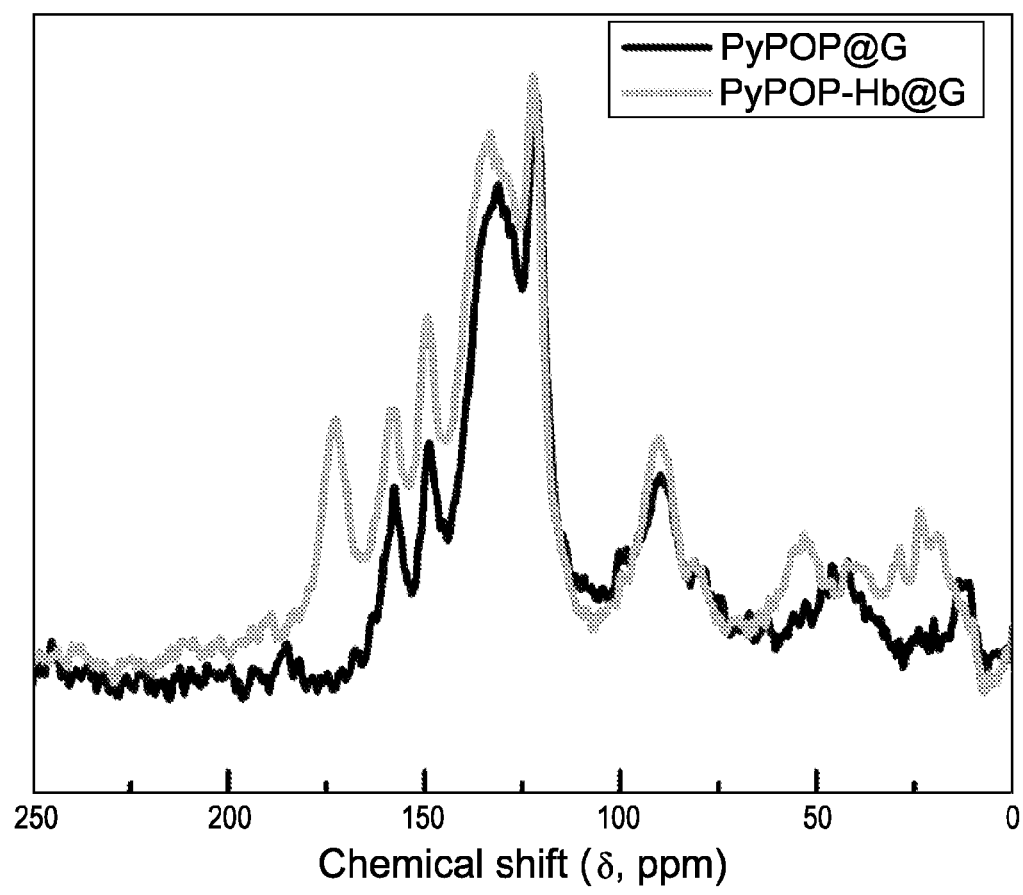
FIG. 3 shows the $^{13}$C-CPMAS NMR spectra of PyPOP@G and PyPOP-Hb@G composites synthesised in Example 1.

The $^{13}$C spectra of PyPOP-Hb@G revealed the presence of resonance peaks at δ 175 ppm, and broad resonance peaks at δ 50 ppm and δ 25 ppm (FIG. 3). Each of these peaks were found to be absent in the $^{13}$C spectrum of PyPOP@G. The additional resonance peaks observed in the PyPOP-Hb@G spectrum were subsequently found to be good agreement with those reported for Hb. This confirmed the presence of immobilised Hb in the PyPOP-Hb@G composite (FIG. 3). The resonance peak at δ 175 ppm was assigned to amide carbonyls, and the peaks at δ 50 ppm and δ 25 ppm to aliphatic groups, of the immobilised Hb proteins. These spectra indicated that Hb had been successfully immobilised within the composite to form PyPOP-Hb@G.

Example 4

Elemental analysis was used to analyse the carbon, nitrogen and oxygen content of each composite synthesised in Example 1, and compared with that of graphene and PyPOP. The results recorded are shown in the table below (Table 1).

TABLE 1

|  | % C | % N | % O |
| --- | --- | --- | --- |
| G | 94.30 | — | — |
| PyPOP | 71.55 | 21.14 | 2.66 |
| PyPOP@G | 76.40 | 6.64 | 2.95 |
| PyPOP-Hb@G | 75.98 | 8.03 | 3.02 |

These data indicated that the carbon content increased when PyPOP@G composites were synthesised from PyPOP. This can be attributed to the incorporation of carbon rich graphene. In addition, the nitrogen content decreased as expected for the same reasons. Elemental analysis of PyPOP-Hb@G revealed an increase in nitrogen content compared to PyPOP@G, consistent with the presence of nitrogen-rich proteins. These data further supported immobilisation of Hb in the PyPOP-Hb@G composition.

Example 5

X-ray photoelectron spectroscopy (XPS) was used to analyse the surface composition of PyPOP-Hb@G, as synthesised in Example 1.

Figure 4:
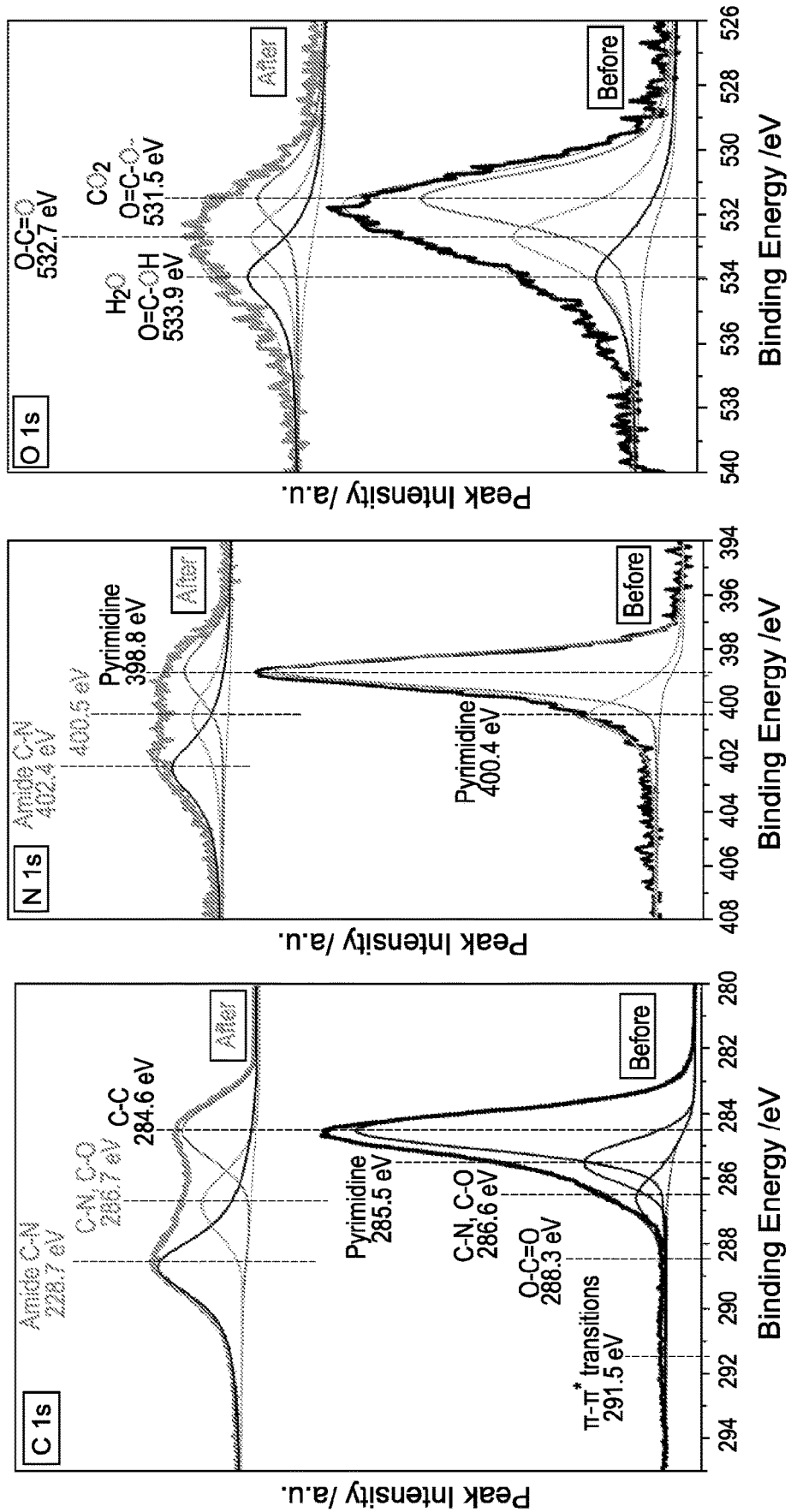
FIG. 4 shows the results of X-ray photoelectron spectroscopy (XPS) analysis (Peak Intensity (a.u.) versus Binding Energy (eV)) of PyPOP-Hb@G synthesised in Example 1.

XPS spectra for the sample were recorded, the sample was then sputtered with Ar ions to probe the composition beneath the surface of the sample, and the spectra recorded again. The binding energies of electrons in the $C^{1s}$, $N^{1s}$ and $O^{1s}$ orbitals before and after sputtering were then plotted (FIG. 4). The $C^{1s}$ spectra revealed distinct peaks at 284.6 eV (corresponding to aromatic C—C bonds), 285.5 and 286.6 eV (corresponding to pyrimidine C—N bonds) and 288.3 eV (corresponding to carbonyl C=O bonds). After sputtering the $C^{1s}$ spectrum revealed the presence of a new peak at 288.7 eV, which was assigned to C—N amide bonds. This binding energy is characteristic of amide bonds in proteins, and indicated that Hb was immobilised within the composite structure, and was not primarily located on the surface. Similar data were recorded in the $N^{1s}$ XPS spectra, wherein after sputtering a new peak at 402.4 eV (C—N amide bonds) was observed, again indicating the presence of Hb within the composite. The $O^{1s}$ XPS spectrum revealed the presence of a peak at 532.6 eV (C—O acid/amide bonds) and 533.9 eV (C—OH acid/water) which increased in intensity following sputtering. Collectively, these data indicated that Hb was immobilised within the PyPOP structure, and hence the characteristic $C^{1s}$ and $N^{1s}$ protein signals were not observed at the composite surface.

Example 6

Scanning electron microscopy (SEM) was used to analyse the surface of PyPOP-Hb@G synthesised in Example 1.

Figure 5:
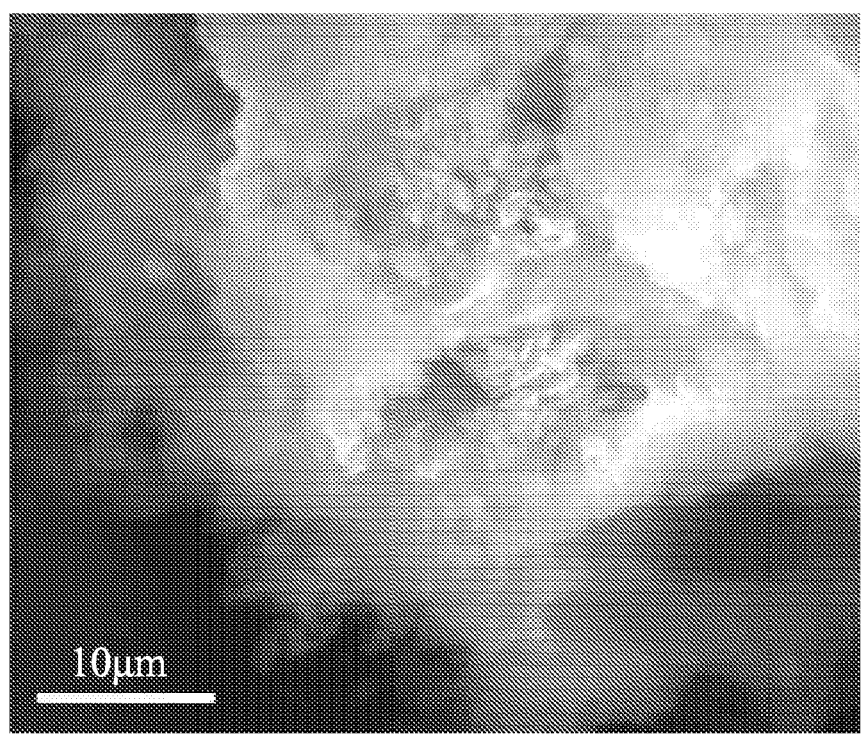
FIG. 5 is a Scanning electron microscopy (SEM) image of the surface of PyPOP-Hb@G synthesised in Example 1.

The SEM image revealed a rough, heterogeneous surface with no discernible segregation between graphene and the POP (FIG. 5).

Example 7

To evaluate the porous structure of the composite synthesised in Example 1, $N_2$ sorption isotherms for each of PyPOP, PyPOP@G and PyPOP-Hb@G were recorded.

Figure 6A:
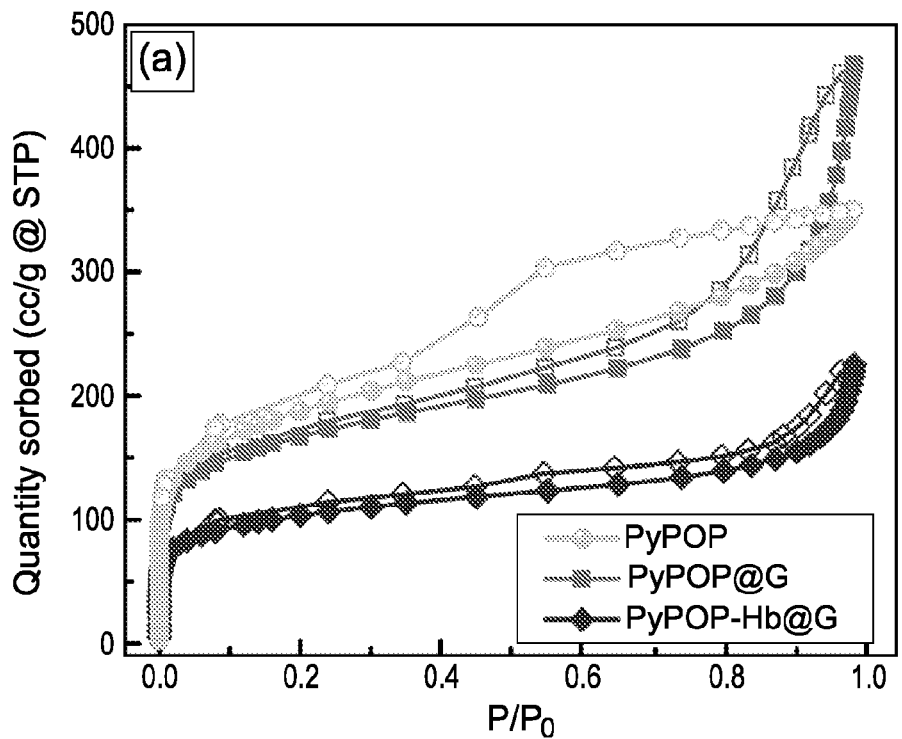
FIG. 6a is $N_2$ gas sorption isotherm for PyPOP, PyPOP@G and PyPOP-Hb@G composites synthesised in Example 1.
Figure 6B:
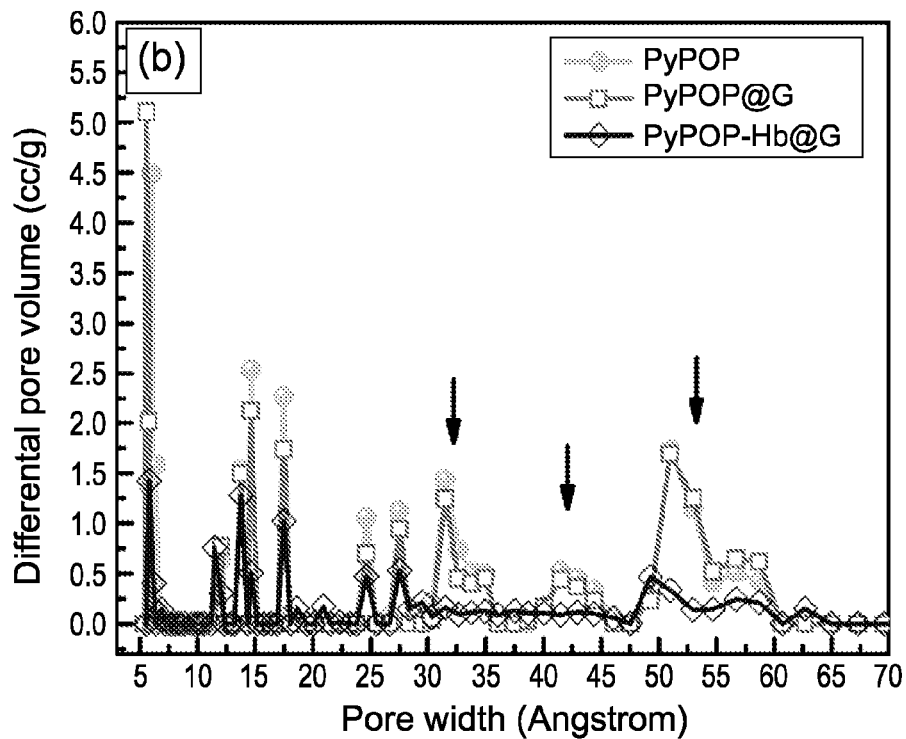
FIG. 6b is a pore size distribution histogram for PyPOP, PyPOP@G and PyPOP-Hb@G composites synthesised in Example 1, with arrows highlighting the most significant differences.

Calculations using the Brauner-Emmet-Teller (BET) model enabled evaluation of the surface area of each sample. BET calculations revealed that each composition had comparable surface areas: PyPOP-Hb@G 445 m$^2$/g; PyPOP@G 582.7 m$^2$/g; and PyPOP 664 m$^2$/g (FIG. 6a). Application of the non-local density function theory (NLDFT) model of carbon finite pores to the early absorption points in the data for each composition allowed the pore size distributions (PSD) to be calculated. Analysis of PyPOP-Hb@G revealed diminished distribution of pores with 32 Å, 42 Å and 50-60 ∪ diameters, as compared to PyPOP and PyPOP@G (FIG. 6b). Cross sections of 49-64 ∪ correspond to that reported for Hb. These data therefore indicate that Hb was occupying correspondingly shaped pores within the PyPOP. The inclusion of Hb within the larger pores may have affected formation of the PyPOP polymer chains, resulting in diminished pores within the 32 ∪ to 42 ∪ range.

Example 8

Cyclic voltammetry (CV) was used to evaluate the utility of PyPOP@G and PyPOP-Hb@G in the oxygen reduction reaction (ORR).

CV was performed using an oxygen-saturated 0.1 M potassium hydroxide solution as the electrolyte, and electrode potentials were recorded using a silver chloride electrode (Ag|AgCl) as a reference, and a carbon paste electrode (CPE) as a control electrode. The oxygen reduction reaction is known to be poor at a CPE, making it an appropriate control.

Figure 7:
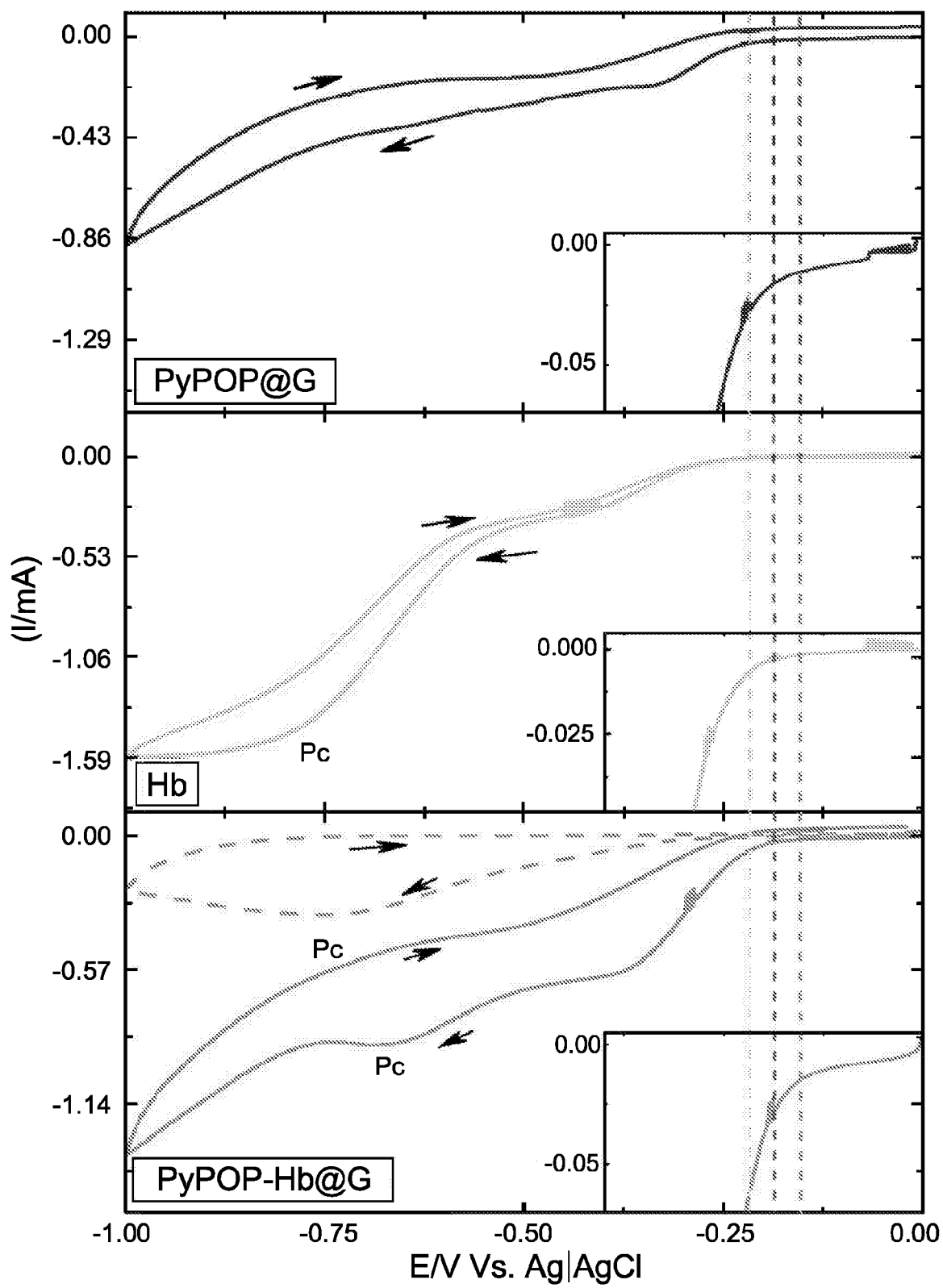
FIG. 7 shows the cyclic voltammetry (CV) cycles for Hb, PyPOP@G and PyPOP-Hb@G composite of the invention, with the inserts showing a magnified portion of the CV indicating the different onset potentials.

Evaluation of PyPOP@G revealed an enhanced reduction onset potential (−0.186 V vs Ag|AgCl) compared to the CPE for the ORR. This observation can be attributed to an increased number of active sites within the porous composite structure for the reaction to occur (FIG. 7). Furthermore, an increase in current density was also observed, which was attributed to the high surface area of the porous composite compared to the reference electrode.

Evaluation of Hb immobilised on CPE in a sol-gel film, under the same conditions, revealed two reduction plateaus with onset potentials of −0.217 V and −0.52 V (vs Ag|AgCl) (FIG. 7). The onset potential at −0.52 V was attributed to reduction of oxygen by the $Fe^{2+}$ haem centre to form $Fe^{3+}$ and superoxide. The second onset potential at −0.217 V was attributed to reduction of $Fe^{3+}$ to $Fe^{2+}$, which overlapped with a second oxygen reduction reaction. The onset potential of the second reduction falls within the range reported for $Hb(Fe^{3+}/Fe^{2+})$ reduction under basic conditions. The cathodic peak $P_c$ for the second reduction is labelled in FIG. 7 at −0.75V, and can therefore be assigned to reduction of $Fe^{3+}$ to $Fe^{2+}$ by peroxide intermediates formed in the first reduction of oxygen.

PyPOP-Hb@G was evaluated under the same electrode configuration. Cyclic voltammetry revealed a considerable enhancement in oxygen reduction activity, demonstrated by an increased current density and a lower onset potential (−0.16 V vs Ag|AgCl), compared to PyPOP@G and Hb. The decrease in onset potential (anodic shift) was attributed to the presence of Hb within the PyPOP pores. PyPOP provides a localised concentration of oxygen i.e. reservoirs of oxygen within the porous structure, and therefore a supply of oxygen is provided in the immediate vicinity of the immobilised Hb. The porphyrin centres of Hb can additionally stimulate the active sites within the PyPOP by readily reacting with, and catalysing the ORR. The high concentration of oxygen trapped within the PyPOP therefore overcomes some unfavourable processes including desolvation of oxygen to reach the active sites.

The onset potential (−0.16 V vs Ag|AgCl, −0.828 vs RHE) for PyPOP-Hb@G in the ORR was found to be comparable to that reported for Platinum on Carbon (0.809 vs RHE), and comparable with various other metal, and non-noble metal, based electrocatalysts. The cathodic peak $P_c$ at −0.676 V was more pronounced for PyPOP-Hb@G compared to that observed for the Hg/CPE electrode. Following degassing of the electrolyte solution, to form an oxygen-free solution, the cathodic peak $P_c$ was still observed (FIG. 7, dashed line). The absence of first onset potential (i.e oxygen reduction and oxidation of $Fe^{2+}$ to $Fe^{3+}$) in the degassed electrolyte can be attributed to rapid reaction of $Fe^{2+}$ with traces of oxygen trapped in the composite, as was observed with the Hb immobilised electrode. The cathodic peak $P_c$ was therefore assigned to the reduction of $Fe^{3+}$ to $Fe^{2+}$. These data further indicated the enhanced catalytic activity of PyPOP-Hb@G in the ORR compared to Hb.

Example 9

Linear sweep voltammetry (LSV) employing the rotating ring disk electrode (RRDE) technique was used to evaluate the mechanism of oxygen reduction on PyPOP-Hb@G.

Figure 8A:
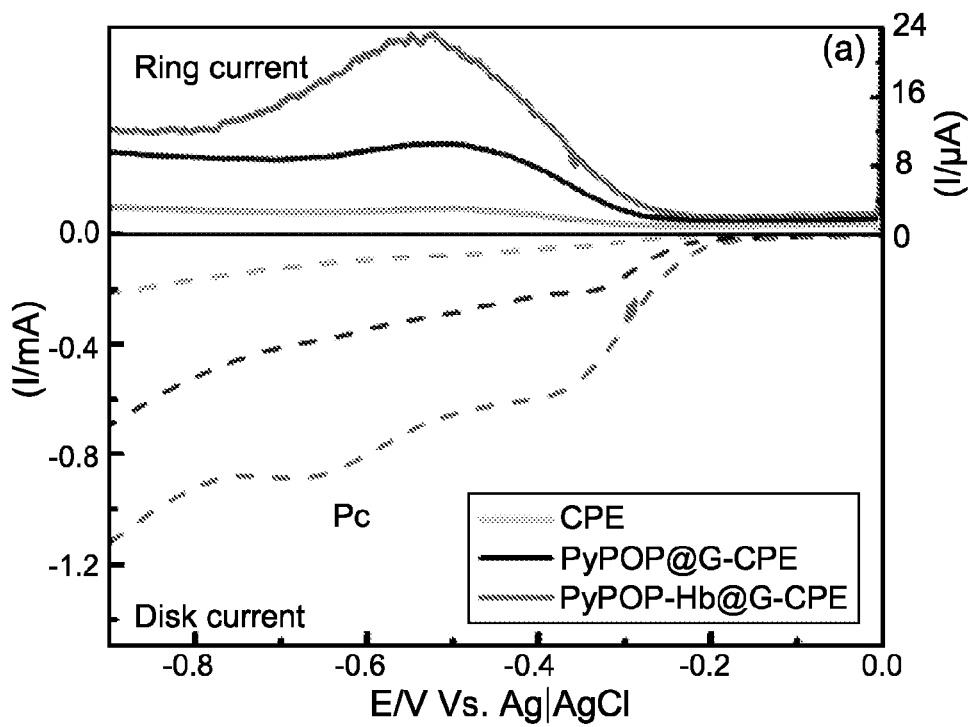
FIG. 8a is an overlay of the disk and ring current Linear Sweep Voltammetry (LSVs) for CPE, PyPOP@G and PyPOP-Hb@G composite.

The oxygen reduction mechanism on porphyrin ($N_4$—Fe) species is reported to proceed via a 4-electron pathway. It was hypothesised that the increased ORR activity of PyPOP-Hb@G, as described in Example 8, was a result of inner sphere electron transfer (ISET) mechanisms facilitated by the porphyrin core of Hb. CPE and PyPOP@G were used as controls. LSVs were recorded at a fixed rotation speed of 1600 rpm, and the electrolyte was an oxygen-saturated 0.1 M potassium hydroxide solution (FIG. 8a).

The disk current observed during the oxygen reduction reaction for CPE and PyPOP@G were both similar, wherein PyPOP@G demonstrated enhanced disk current attributed to the larger surface area of the porous structure. The enhanced ring current observed for PyPOP@G compared to CPE was attributed to enhanced production and oxidation of hydrogen peroxide. In comparison PyPOP-Hb@G demonstrated a reduced onset potential for the disk current, associated with the presence of immobilised Hb in the porous structure, and an increased ring current, associated with greater ORR activity. These data are in support of the data described in Example 8.

Figure 8B:
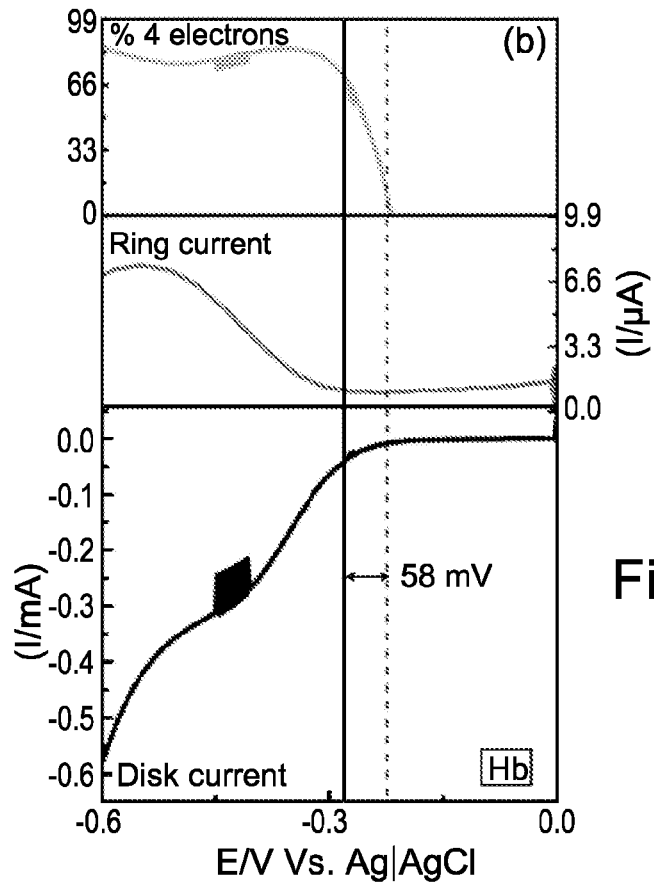
FIGS. 8b-8d are the LSVs and % 4 electron for (b) Hb, (c) PyPOP@G and (d) PyPOP-Hb@G
Figure 8C:
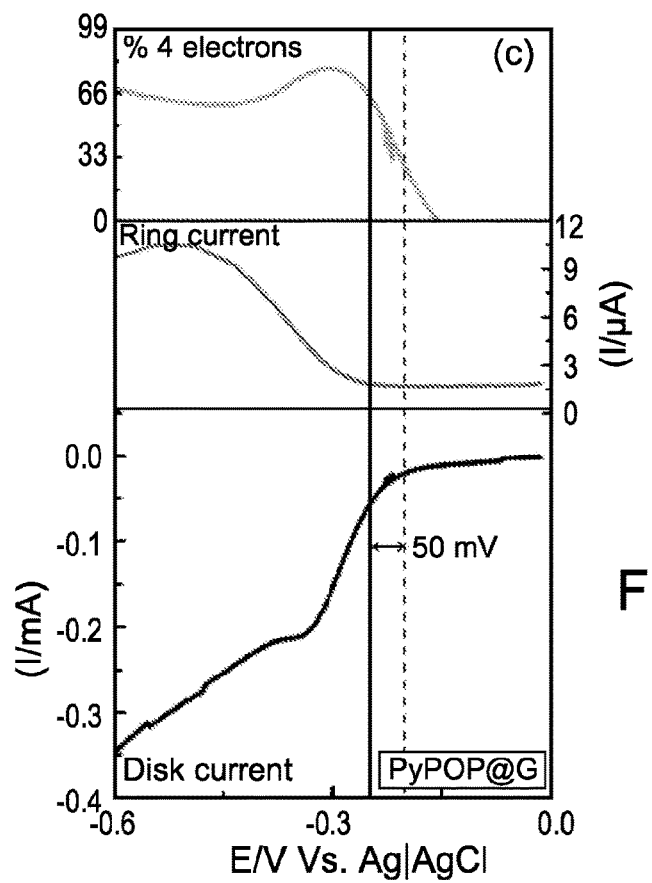
Figure 8D:
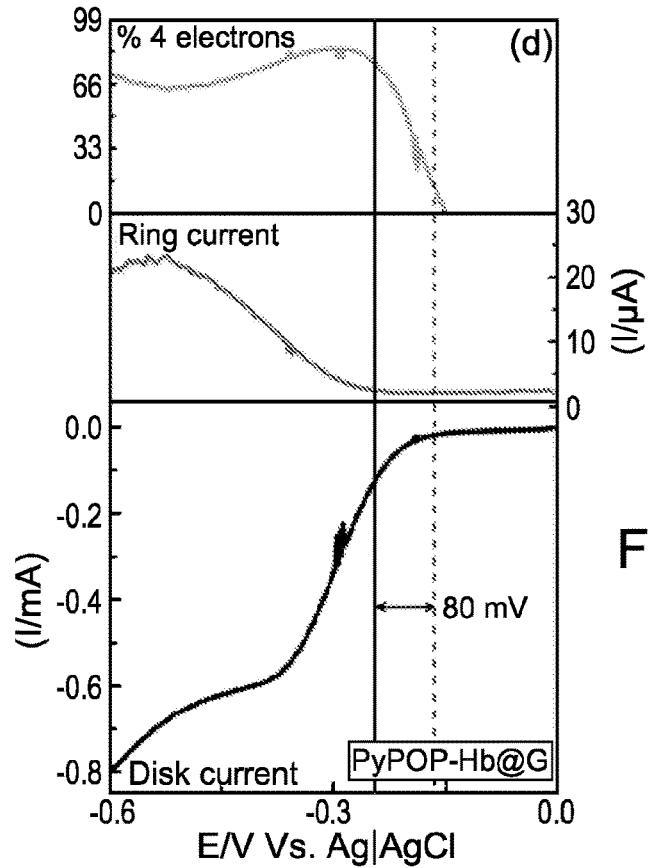

Utilising both the ring current and disk current recorded, the proportion of the current consumed in a 4-electron oxygen reduction pathway was calculated (FIGS. 8b-d). Interestingly, for each of CPE, PyPOP@G and PyPOP-Hb@G, the ring current and disk current were shown to have an inverse relationship as the voltage was increased. The area between the onset potential of the ring current and the onset potential of the disk current indicated the onset of the 4-electron pathway through the ISET mechanism (FIG. 8b-d). The difference in voltage ($\Delta E$) between the onset potential of the ring current, and the onset potential of the disk current therefore provided a voltage range in which onset of the 4-electron pathway became the dominant reduction pathway. PyPOP-Hb@G ($\Delta E=80$ mV) demonstrated an earlier onset of the 4-electron ISET mechanism compared to PyPOP ($\Delta E=50$ mV) and Hb ($\Delta E=58$ mV) (FIG. 8b-d). These data suggest that a synergy between PyPOP and Hb resulted in enhancement of 4-electron ISET activity on PyPOP-Hb@G, compared to PyPOP or Hb alone.

Example 10

To further evaluate the ORR mechanism on PyPOP-Hb@G, LSVs utilising the rotating disk electrode (RDE) technique were performed, under variable disk rotation speeds. The CPE and PyPOP@G demonstrated no disk current dependence on the rate of rotation (FIG. 8a, area A), and can therefore be attributed to a kinetically controlled ORR. However, at increased voltages (FIG. 8a, area B), the charge transfer was enhanced, and the ORR became an oxygen-diffusion controlled process. As porous PyPOP@G has a larger surface area compared to CPE, and therefore greater capacity to store oxygen therein, PyPOP@G demonstrated enhanced disk current at higher voltages.

The disk current recorded for the ORR over the Hb and PyPOP-Hb@G electrode surfaces were shown to depend on the disk rotation speed for potentials in area A (FIG. 8b-c). The relationship between disk current and disk rotation speed was more pronounced for the PyPOP-Hb@G electrode compared to the Hb electrode alone. These data indicated synergism between the Hb and PyPOP, wherein PyPOP acts as an oxygen reservoir to supply Hb, thereby enhancing the ORR. The Koutecky-Levich equation ($B=0.62nFC_oD_o^{2/3}v^{-1/6}$ wherein n=number of electrons) was then applied to the PyPOP-Hb@G LSV RDE curves to plot a linear graph. The value of n, the number of electrons involved in the ORR, was then calculated using the Koutecky-Levich plot to be 4, consistent with the more-efficient 4-electron ORR pathway.

The invention claimed is:

1. A composite comprising graphene, a metalloprotein and a conjugated porous organic polymer, wherein said conjugated porous organic polymer comprises a repeat unit of monomer (IVa) or monomer (IVc):

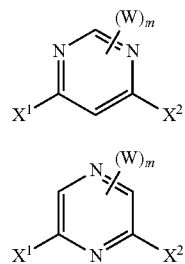

wherein:
$X_1$ is selected from halide, OH or OTf;
$X_2$ is selected from halide, OH, OTf and alkynyl;
each W is independently selected from alkynyl, halide, OH, OTf, CHO, COR, COOR, COOH, $NH_2$, NHR, $NR_2$, CONH, CONHR wherein R is $C_{1-8}$ alkyl, OH, phenol, halide, aryl or heteroaryl; and
m is 0 or an integer between 1 and 4.

2. A composite as claimed in claim 1, wherein said conjugated porous organic polymer is distributed on the surface of said graphene.

3. A composite as claimed in claim 1, wherein said metalloprotein is encapsulated in said conjugated porous organic polymer in said composite.

4. A composite as claimed in claim 1, wherein said conjugated porous organic polymer further comprises a repeat unit derived from a monomer of formula (II):

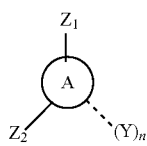

wherein
A is an aromatic ring or ring system;
$Z_1$ is alkynyl;
$Z_2$ is selected from alkynyl, halide, OH and OTf;
---- is a bond which may be present or absent;
each Y is independently selected from alkynyl, halide, OH, OTf, CHO, COR, COOR, COOH, $NH_2$, NHR, $NR_2$, CONH, CONHR wherein R is $C_{1-8}$ alkyl, OH, phenol, halide, aryl or heteroaryl, and
n is 0 or an integer between 1 and 4.

5. A composite as claimed in claim 4, wherein $Z_1$, $Z_2$ and Y are all alkynyl.

6. A composite as claimed in claim 1, wherein each W is selected from halide, OH and OTf; and m is 0 or 1.

7. A composite as claimed in claim 1, wherein $X_1$ and $X_2$ are the same.

8. A composite as claimed in claim 1, wherein $X_1$ and $X_2$ are selected from halide, OH and OTf.

9. A composite as claimed in claim 6, wherein said monomer of formula (IVa) is:

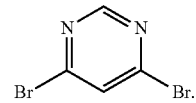

10. A composite as claimed in claim 1, further comprising a unit derived from a compound of formula (VI):

wherein
C is an aromatic ring or ring system;
U is selected from halide, OH or OTf;
---- is a bond which may be present or absent;
V is selected from CHO, COR, COOR, COOH, $NH_2$, NHR, $NR_2$, CONH, CONHR wherein R is $C_{1-8}$ alkyl, OH, phenol, halide, aryl or heteroaryl; and
is 0 or an integer between 1 and 4.

11. A composite as claimed in claim 10, wherein said unit of formula (VI) is selected from monomers (VIa), (VIb), (VIc) and (VId):

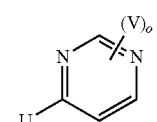

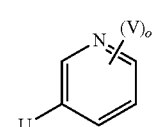

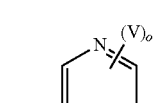

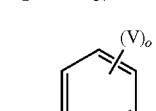

wherein U, V and o are as defined in claim 10.

12. A composite as claimed in claim 1, wherein said graphene has an average particle size of 50 nm to 50 micron.

13. A composite as claimed in claim 1, wherein said metalloprotein is a haemoprotein.

14. A method of making a composite as claimed in claim 1 comprising
mixing graphene, a metalloprotein and a conjugated porous organic polymer.

15. A method as claimed in claim 14, comprising:
mixing graphene, a metalloprotein and monomers for the preparation of a conjugated porous organic polymer in the presence of a catalyst to form a composite; and
obtaining said composite.

16. An article comprising a composite as claimed in claim 1.

17. A medical device comprising an electrode which comprises claim 1.

18. A method of catalysing an oxygen reduction reaction comprising: bringing a material to be oxidised into contact with an electrode comprising a composite as claimed in claim 1.

19. A composite as claimed in claim 4, wherein said monomer of formula (II) is selected from monomers (IIa), (IIb) and (IIc):

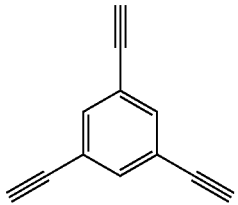

(IIa)

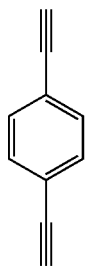

(IIb)

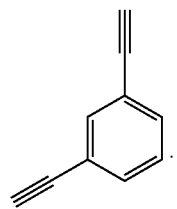

(IIc)

20. A composite as claimed in claim 4, wherein said monomer of formula (II) is monomer (IIa):

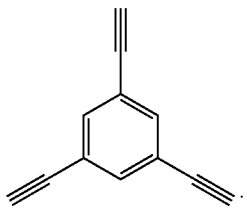

(IIa)

* * * * *